US010119055B2

(12) United States Patent
Boussand

(10) Patent No.: US 10,119,055 B2
(45) Date of Patent: Nov. 6, 2018

(54) STABLE 2,3,3,3-TETRAFLUOROPROPENE COMPOSITION

(71) Applicant: Arkema France, Colombes (FR)

(72) Inventor: Beatrice Boussand, Sainte Foy les Lyon (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/990,159

(22) Filed: Jan. 7, 2016

(65) Prior Publication Data

US 2016/0115361 A1 Apr. 28, 2016

Related U.S. Application Data

(62) Division of application No. 13/808,326, filed as application No. PCT/FR2011/051406 on Jun. 20, 2011.

(60) Provisional application No. 61/364,539, filed on Jul. 15, 2010.

(30) Foreign Application Priority Data

Jul. 9, 2010 (FR) ..................... 10 55628

(51) Int. Cl.
*C09K 5/04* (2006.01)
*C07C 21/18* (2006.01)
*C10M 171/00* (2006.01)

(52) U.S. Cl.
CPC ............. *C09K 5/04* (2013.01); *C07C 21/18* (2013.01); *C09K 5/045* (2013.01); *C10M 171/008* (2013.01); *C09K 2205/126* (2013.01); *C09K 2205/22* (2013.01); *C10M 2207/2835* (2013.01); *C10M 2209/043* (2013.01); *C10M 2209/1033* (2013.01); *C10N 2220/302* (2013.01); *C10N 2230/08* (2013.01); *C10N 2240/30* (2013.01)

(58) Field of Classification Search
CPC .............. C09K 5/045; C09K 2205/126; C09K 2205/22
See application file for complete search history.

(56) References Cited

U.S. PATENT DOCUMENTS

| | | | |
|---|---|---|---|
| 5,895,778 A | 4/1999 | McHenry et al. | |
| 7,534,366 B2 | 5/2009 | Singh et al. | |
| 7,795,480 B2 | 9/2010 | Merkel et al. | |
| 8,058,486 B2 * | 11/2011 | Merkel | C01B 7/035 570/135 |
| 8,070,977 B2 | 12/2011 | Rached | |
| 8,075,798 B2 | 12/2011 | Rached | |
| 8,217,208 B2 | 7/2012 | Hulse et al. | |
| 8,246,850 B2 | 8/2012 | Rached | |
| 8,252,198 B2 | 8/2012 | Rached | |
| 8,557,135 B2 | 10/2013 | Rached | |
| 8,808,569 B2 | 8/2014 | Rached | |
| 8,858,824 B2 | 10/2014 | Boussand | |
| 8,858,825 B2 | 10/2014 | Guerin et al. | |
| 9,011,711 B2 | 4/2015 | Rached | |
| 9,028,706 B2 | 5/2015 | Rached et al. | |
| 9,039,922 B2 | 5/2015 | Rached | |
| 9,127,191 B2 | 9/2015 | Rached | |
| 9,133,379 B2 | 9/2015 | Rached | |
| 9,175,203 B2 | 11/2015 | Rached | |
| 9,267,064 B2 | 2/2016 | Rached | |
| 9,315,708 B2 | 4/2016 | Guerin et al. | |
| 9,399,726 B2 | 7/2016 | Rached | |
| 9,505,968 B2 | 11/2016 | Rached | |
| 9,512,343 B2 | 12/2016 | Rached et al. | |
| 9,599,381 B2 | 3/2017 | Rached | |
| 9,650,551 B2 | 5/2017 | Collier et al. | |
| 9,650,553 B2 | 5/2017 | Deur-Bert et al. | |
| 9,663,697 B2 | 5/2017 | Rached | |
| 9,676,984 B2 | 6/2017 | Guerin et al. | |
| 9,683,155 B2 | 6/2017 | Deur-Bert et al. | |
| 9,683,157 B2 | 6/2017 | Rached | |
| 9,884,984 B2 | 2/2018 | Rached | |
| 9,908,828 B2 | 3/2018 | Rached et al. | |
| 9,969,918 B2 | 5/2018 | Deur-Bert et al. | |
| 10,023,780 B2 | 7/2018 | Guerin et al. | |
| 10,035,938 B2 | 7/2018 | Rached | |

(Continued)

FOREIGN PATENT DOCUMENTS

EP 2 119 759 A1 11/2009
EP 2 149 543 A1 2/2010
(Continued)

OTHER PUBLICATIONS

Knunyants, I.L., et al., Reactions of Fluoroolefins Communication 13. Catalytic Hydrogenation of Perfluoroolefins, Institute of Hetroorganic Compounds, Academy of Sciences of the USSR, No. 8, Aug. 1960, pp. 1412-1418.
Boussand, Béatrice, U.S. Appl. No. 14/371,118 entitled "Heat Transfer Compositions Having Improved Miscibility With Lubricating Oil," filed Jul. 8, 2014.
Rached, Wissam, U.S. Appl. No. 14/615,741 entitled "Heat Transfer Fluid Replacing R-410A," filed Feb. 6, 2015.
Rached, Wissam, U.S. Appl. No. 14/615,780 entitled "Low-Temperature and Average-Temperature Refrigeration," filed Feb. 6, 2015.
International Search Report issued in PCT/FR2011/051406, dated Jan. 25, 2012, 7 pages, European Patent Office, Rijswijk, NL (English and French language versions).
(Continued)

*Primary Examiner* — John R Hardee
(74) *Attorney, Agent, or Firm* — Buchanan Ingersoll & Rooney P.C.

(57) ABSTRACT

A stable composition (CS) including at least x wt.-% 2,3,3,3-tetrafluoropropene (99.8 ≤ x<100), at most y wt.-% unsaturated compound(s) (Ia) (0<y ≤ 0.2) selected from among 3,3,3-trifluoropropene (HFO-1243zf) and the positional isomers of 2,3,3,3-tetrafluoropropene, such as 1,3,3,3-tetrafluoropropene (isomers Z and E) and 1,1,2,3-tetrafluoropropene, and, optionally, at most 500 ppm of 3,3,3-trifluoropropyne and/or at most 200 ppm 1,1,1,2,3-pentafluoropropene (HFO-1225ye).

26 Claims, No Drawings

(56) References Cited

U.S. PATENT DOCUMENTS

| | | |
|---|---|---|
| 2004/0256594 A1 | 12/2004 | Singh et al. |
| 2006/0243944 A1 | 11/2006 | Minor et al. |
| 2006/0243945 A1 | 11/2006 | Minor et al. |
| 2008/0111099 A1 | 5/2008 | Singh et al. |
| 2008/0135817 A1 | 6/2008 | Luly et al. |
| 2008/0230738 A1 | 9/2008 | Minor et al. |
| 2009/0030247 A1 | 1/2009 | Johnson et al. |
| 2010/0012882 A1 | 1/2010 | Sherman et al. |
| 2010/0029997 A1 | 2/2010 | Wang et al. |
| 2010/0038582 A1 | 2/2010 | Shimomura et al. |
| 2010/0119460 A1 | 5/2010 | Pham et al. |
| 2010/0181524 A1 | 7/2010 | Elsheikh et al. |
| 2010/0205980 A1 | 8/2010 | Dixon et al. |
| 2010/0301259 A1 | 12/2010 | Leck et al. |
| 2011/0021849 A1 | 1/2011 | Avril et al. |
| 2011/0041530 A1 | 2/2011 | Mouli et al. |
| 2011/0084228 A1 | 4/2011 | Rached |
| 2011/0095224 A1 | 4/2011 | Rached |
| 2011/0186772 A1 | 8/2011 | Rached |
| 2011/0197602 A1 | 8/2011 | Abbas |
| 2011/0219791 A1 | 9/2011 | Rached |
| 2011/0219792 A1 | 9/2011 | Rached |
| 2011/0240254 A1 | 10/2011 | Rached |
| 2011/0284181 A1 | 11/2011 | Rached |
| 2012/0049104 A1 | 3/2012 | Rached |
| 2012/0056123 A1 | 3/2012 | Rached |
| 2012/0065437 A1 | 3/2012 | Merkel |
| 2012/0068105 A1 | 3/2012 | Rached et al. |
| 2012/0128964 A1 | 5/2012 | Hulse |
| 2012/0144857 A1 | 6/2012 | Rached |
| 2012/0151958 A1 | 6/2012 | Rached |
| 2012/0151959 A1 | 6/2012 | Rached |
| 2012/0153213 A1 | 6/2012 | Rached |
| 2012/0159982 A1 | 6/2012 | Rached |
| 2012/0161063 A1 | 6/2012 | Singh |
| 2012/0161064 A1 | 6/2012 | Rached |
| 2012/0167615 A1 | 7/2012 | Rached |
| 2012/0205574 A1 | 8/2012 | Rached et al. |
| 2012/0226081 A1 | 9/2012 | Elsheikh et al. |
| 2013/0004435 A1 | 1/2013 | Cook et al. |
| 2013/0092869 A1 | 4/2013 | Boussand |
| 2013/0105724 A1 | 5/2013 | Boussand |
| 2013/0186114 A1 | 7/2013 | Guerin et al. |
| 2014/0008565 A1 | 1/2014 | Rached et al. |
| 2014/0075969 A1 | 3/2014 | Guerin et al. |
| 2014/0318160 A1 | 10/2014 | Rached |
| 2014/0326017 A1 | 11/2014 | Rached |
| 2015/0027146 A1 | 1/2015 | Boussand |
| 2015/0034523 A1 | 2/2015 | Kopkalli et al. |
| 2015/0152306 A1 | 6/2015 | Rached |
| 2015/0152307 A1 | 6/2015 | Rached |
| 2015/0322317 A1 | 11/2015 | Collier et al. |
| 2015/0322321 A1 | 11/2015 | Deur-Bert et al. |
| 2015/0344761 A1 | 12/2015 | Rached |
| 2015/0353799 A1 | 12/2015 | Deur-Bert et al. |
| 2015/0353802 A1 | 12/2015 | Rached |
| 2016/0009555 A1 | 1/2016 | Bonnet et al. |
| 2016/0024363 A1 | 1/2016 | Rached |
| 2016/0025394 A1 | 1/2016 | Rached |
| 2016/0122609 A1 | 5/2016 | Rached |
| 2016/0194541 A1 | 7/2016 | Guerin et al. |
| 2016/0244652 A1 | 8/2016 | Rached |
| 2016/0272561 A1 | 9/2016 | Rached et al. |
| 2016/0298014 A1 | 10/2016 | Rached |
| 2016/0355718 A1 | 12/2016 | Rached |
| 2016/0376484 A1 | 12/2016 | Guerin et al. |
| 2017/0037291 A1 | 2/2017 | Rached et al. |
| 2017/0080773 A1 | 3/2017 | Rached |
| 2017/0145276 A1 | 5/2017 | Rached |
| 2017/0210960 A1 | 7/2017 | Deur-Bert et al. |
| 2017/0210962 A1 | 7/2017 | Collier et al. |
| 2017/0218241 A1 | 8/2017 | Deur-Bert et al. |
| 2017/0218242 A1 | 8/2017 | Rached |
| 2018/0086173 A1 | 3/2018 | Rached |
| 2018/0134936 A1 | 5/2018 | Rached |
| 2018/0148395 A1 | 5/2018 | Rached et al. |

FOREIGN PATENT DOCUMENTS

| | | |
|---|---|---|
| EP | 2 281 792 A1 | 2/2011 |
| JP | H4-110388 | 4/1992 |
| JP | H04-110388 | 4/1992 |
| JP | 2008/531836 A | 8/2008 |
| JP | 2010-133401 A | 6/2010 |
| WO | WO 2007/126414 A2 | 11/2007 |
| WO | WO 2007/126414 A3 | 11/2007 |
| WO | WO 2008/027515 A2 | 3/2008 |
| WO | WO 2008/027515 A3 | 3/2008 |
| WO | WO 2008/027516 A1 | 3/2008 |
| WO | WO 2008/027596 A2 | 3/2008 |
| WO | WO 2008/030439 A2 | 3/2008 |
| WO | WO 2008/030440 A2 | 3/2008 |
| WO | WO 2008/042066 A1 | 4/2008 |
| WO | WO 2009/003165 A1 | 12/2008 |
| WO | WO 2009/137656 A1 | 11/2009 |
| WO | WO 2010/029704 A1 | 3/2010 |
| WO | WO 2010/043807 A1 | 4/2010 |
| WO | WO 2010/056695 A2 | 5/2010 |
| WO | WO 2010/056695 A3 | 5/2010 |
| WO | WO 2010/059677 A2 | 5/2010 |
| WO | WO 2010/064011 A1 | 6/2010 |
| WO | 2010/075046 A2 | 7/2010 |
| WO | WO 2012/004487 A2 | 1/2012 |
| WO | WO 2012/004487 A3 | 1/2012 |
| WO | WO 2014/158663 A1 | 10/2014 |
| WO | 2010/008640 A1 | 1/2016 |

OTHER PUBLICATIONS

Collier, Bertrand, et al., U.S. Appl. No. 14/651,855 entitled "Composition Including 2,3,3,3-Tetrafluoropropene," filed Jun. 12, 2015.
Deur-Bert, Dominique, et al., U.S. Appl. No. 14/651,925 entitled "Composition Containing 2,3,3,3-Tetrafluoropropene and 1,2-Difluoroethylene," filed Jun. 12, 2015.
Deur-Bert, Dominique, et al., U.S. Appl. No. 14/655,500 entitled "Azeotropic or Quasi-Azeotropic Composition of Chloromethane," filed Jun. 25, 2015.
Rached, Wissam, U.S. Appl. No. 14/823,430 entitled "Use of Ternary Compositions," filed Aug. 11, 2015.
Rached, Wissam, U.S. Appl. No. 14/830,130 entitled "Binary Refrigerating Fluid," filed Aug. 19, 2015.
Bonnet, Phillippe, et al., U.S. Appl. No. 14/772,950 entitled "Composition Comprising HF and 2,3,3,3-Tetrafluoropropene," filed Sep. 4, 2015.
Rached, Wissam, U.S. Appl. No. 14/873,855 entitled "Heat Transfer Fluid," filed Oct. 2, 2015.
Rached, Wissam, U.S. Appl. No. 14/873,891 entitled "Ternary Compositions for Low-Capacity Refrigeration," filed Oct. 2, 2015.
Guérin, Sophie, et al., U.S. Appl. No. 14/903,461 entitled, "2,3,3,3-Tetrafluoropropene Compositions Having Improved Miscibility," filed Jan. 7, 2016.
Rached, Wissam, U.S. Appl. No. 14/922,387 entitled, "Ternary Compositions for High-Capacity Refrigeration," filed Jan. 11, 2016.
Guerin, Sophie, et al., U.S. Appl. No. 15/070,955, entitled "Heat-Transfer Compositions Exhibiting Improved Miscibility with the Lubricating Oil,"filed Mar. 15, 2016.
Rached, Wissam, et al., U.S. Appl. No. 15/073,108 entitled "Stabilization of 1-Chloro-3,3,3-Trifluoropropenr," filed Mar. 17, 2016.
Rached, Wissam, U.S. Appl. No. 15/238,883 entitled "Heat Transfer Fluid REplacing R-134a," filed Aug. 17, 2016.
Rached, Wissam, et al., U.S. Appl. No. 15/297,569 entitled "Composition Based 2,3,3,3-Tetrafluoropropene," filed Oct. 19, 2016.
Rached, Wissam, et al., U.S. Appl. No. 15/368,347 entitled "Vehicle Heating and/or Air Conditioning Method", filed Dec. 2, 2016.
Rached, Wissam, U.S. Appl. No. 15/396,855 entitled "Heat Transfer Fluid," filed Jan. 3, 2017.
Notice of Opposition to a European Patent, Opposed Patent EP 2 590 916; Opponent: Mexichem Fluor S.A. de C.V., Jul. 11, 2017, 19 pages.

(56) References Cited

OTHER PUBLICATIONS

French Patent Application No. 0955139 filed Jul. 23, 2009, dated Jun. 3, 2010, 28 pages, INPI, Paris, FR [Mexichem Opposition Doc No. D5P].
Notice of Opposition to a European Patent, Opposed Patent: EP 2 590 916: Opponent: The Chemours Company FC, LLC, Jul. 12, 2017, 18 pages.
Chart of Gardner Color Scale, 1 page [Chemours Opposition Doc No. D4].
Declaration by the inventor Béatrice Boussand in U.S. Appl. No. 13/808,326, Apr. 30, 2015, 4 pages [Chemours Opposition Doc No. D5].
Notice of Opposition against EP 2 590 916 B1 on behalf of Daikin Industries, Ltd., Jul. 12, 2017, 10 pages.
Experimental Report prepared by Opponent, Notice of Opposition by Daikin Industries of Jul. 12, 2017, 7 pages [Daikin Opposition Doc No. D4].
Harp International, Safety Data Sheet According to Regulation (EC) No. 1907/2006- HARP® HFO-1234yf, Feb. 2012, Version: CLP016 pp. (1-6), Harp International Ltd., England & Wales, UK; http://www.harpintl.com/downloads/pdf/msds/harp-hfo-1234yf-clp.pdf [Daikin Opposition Doc No. D5].
Honeywell Fluorine Products, Honeywell HFO-1234ze Blowing Agent, Oct. 2008, 3 pages, Honeywell International Inc.; https://www51.honeywell.com/sm/lgwp-fr/common/documents/FP_LGWP_FR_Honeywell-HFO-1234ze_Literature_documentpdf [Daikin Opposition Doc No. D6].
Decision to Decline the Amendment issued in JP Patent Application No. 2013-519 130, Jun. 30, 2017, 4 pages, Japanese Patent Office (JP and English-language translation).
Decision of Refusal, issued in JP Patent Application No. 2013-519 130, Jun. 30, 2017, 2 pages, Japanese Patent Office (JP and English-language translation).
English-language Translation of Third Party IDS filed in JP Patent Application No. 2013-519130, Jun. 2, 2017, 5 pages, author unknown.
Rached, Wissam, U.S. Appl. No. 15/820,996 entitled "Method for Heating and/or Air Conditioning a Vehicle," filed in the U.S. Patent and Trademark Office on Nov. 22, 2017.
Rached, Wissam, U.S. Appl. No. 15/856,703 entitled "Binary Refrigerating Fluid," filed in the U.S. Patent and Trademark Office on Dec. 28, 2017.
Rached, Wissam, U.S. Appl. No. 15/878,794 entitled "Stabilization of 1-Chloro-3,3,3-Trifluoropropene," filed in the U.S. Patent and Trademark Office on Jan. 24, 2018.
Office Action dated Dec. 28, 2017 by the Japanese Patent Office in corresponding Japanese Patent Application No. 2013-519130. (13 pages).
Office Action, issued by the Japanese Intellectual Property Office in JP Patent Application 2013-519130, dated Jun. 22, 2018, 13 pages.
Office Action, issued by the Japanese Intellectual Property Office in JP Patent Application No. 2013-519130, dated Dec. 28, 2017, with English-language translation, 6 pages.
Guerin, Sophie, et al., U.S. Appl. No. 15/997,077 entitled "2,3,3,3-Tetrafluoropropene Compositions Having Improved Miscibility," filed in the U.S. Patent and Trademark Office on Jun. 4, 2018.
Boussand, Beatrice, U.S. Appl. No. 16/034,539 entitled "Stable 2,3,3,3-Tetrafluoropropene Composition," filed in the U.S. Patent and Trademark Office on Jul. 13, 2018.

\* cited by examiner

STABLE 2,3,3,3-TETRAFLUOROPROPENE COMPOSITION

CROSS REFERENCE TO RELATED APPLICATIONS

The present application is a continuation of U.S. application Ser. No. 13/808,326, filed on Jan. 1, 2013, which is U.S. national stage application of International Application No. PCT/FR2011/051406, filed on Jun. 20, 2011, which claims the benefit of U.S. Provisional Application No. 61/364,539, filed on Jul. 15, 2010, and which claims the benefit of French Application No. 1055628, filed on Jul. 9, 2010. The entire contents of each of U.S. application Ser. No. 13/808,326, International Application No. PCT/FR2011/051406, U.S. Provisional Application No. 61/364,539, and French Application No. 1055628 are hereby incorporated herein by reference in their entirety.

TECHNICAL FIELD

The present invention relates to a stable composition including 2,3,3,3-tetrafluoropropene capable of being used in refrigeration and air conditioning.

BACKGROUND

The problems presented by substances which deplete the atmospheric ozone layer were dealt with at Montreal, where the protocol was signed imposing a reduction on the production and use of chlorofluorocarbons (CFCs). This protocol has formed the subject of amendments which have required the abandoning of CFCs and have extended regulation to other products, including hydrochlorofluorocarbons (HCFCs).

The refrigeration and air conditioning industries have invested a great deal in the replacement of these refrigerants and it is because of this that hydrofluorocarbons (HFCs) have been marketed.

In the motor vehicle industry, the air conditioning systems of commercial vehicles have been changed in many countries from a refrigerant comprising chlorofluorocarbon (CFC-12) to that of hydrofluorocarbon (1,1,1,2-tetrafluoroethane: HFC-134a), which is less harmful to the ozone layer. However, from the viewpoint of the objectives set by the Kyoto protocol, HFC-134a (GWP=1430) is regarded as having a high heating power. The contribution to the greenhouse effect of a refrigerant is quantified by a criterion, the GWP (Global Warming Potential), which summarizes the heating power by taking a reference value of 1 for carbon dioxide.

Hydrofluoroolefins (HFOs) have a low heating power and thus meet the objectives set by the Kyoto protocol. The document JP 4-110388 discloses 2,3,3,3-tetrafluoropropene (HFO-1234yf) as heat transfer agent in refrigeration, air conditioning and heat pumps.

In addition to having good properties as a heat transfer agent, in order for a refrigerant to be accepted commercially, it must in particular be thermally stable and be compatible with lubricants. This is because it is highly desirable for the refrigerant to be compatible with a lubricant used in the compressor present in the majority of refrigeration systems. This refrigerant and lubricant combination is important for the use and the effectiveness of the refrigeration system; in particular, the lubricant has to be sufficiently soluble in the refrigerant throughout the operating temperature range.

According to the document WO 2008/042066, as fluoroolefins are capable of decomposing on contact with moisture, oxygen or other compounds when they are used as refrigerant, possibly at high temperature, it is recommended to stabilize them with at least one amine.

Other stabilizing agents, such as benzophenone derivatives, lactones and some phosphorus-comprising compounds, have also been proposed for stabilizing fluoroolefins (WO 2008/027596, WO 2008/027516 and WO 2008/027515).

Furthermore, the document EP 2 149 543 describes a process for the purification of 1,1,1,2,3-pentafluoropropane, a starting material in the manufacture of HFO-1234yf, in order to obtain a product having a 1,1,1,2,3-pentafluoropropene (HFO-1225ye) content of less than 500 ppm and a trifluoropropyne content of less than 50 ppm.

DETAILED DESCRIPTION

The Applicant Company has now developed a 2,3,3,3-tetrafluoropropene composition which makes it possible to improve the thermal stability when it is used in refrigeration systems.

A subject-matter of the present invention is thus a stable composition (SC) comprising at least x % by weight of 2,3,3,3-tetrafluoropropene ($99.8 \leq x < 100$), at most y % by weight of unsaturated compound(s) (Ia) ($0 < y \leq 0.2$) chosen from 3,3,3-trifluoropropene (HFO-1243zf) and the positional isomers of 2,3,3,3-tetrafluoropropene, such as 1,3,3,3-tetrafluoropropene (Z and E isomers) and 1,1,2,3-tetrafluoropropene, and optionally at most 500 ppm of 3,3,3-trifluoropropyne and/or at most 200 ppm of 1,1,1,2,3-pentafluoropropene (HFO-1225ye).

The stable composition according to the present invention can additionally comprise at least one of the compounds (Ib) chosen from 1,1,1,2-tetrafluoropropane (HFC-254eb), 1,1,1,2,3-pentafluoropropane (HFC-245eb), 1,1,1,2-tetrafluoroethane (HFC-134a), 1,1,2-trifluoroethane (HFC-143), 1,1,1,2,3,3-hexafluoropropane, hexafluoropropene, cyclohexafluoropropene and 1,1,1,3,3-pentafluoropropene (HFO-1225zc).

The combined compounds (Ib) present in the composition according to the present invention represent at most 500 ppm.

Preferably, the SC composition comprises at least 99.85% by weight of 2,3,3,3-tetrafluoropropene, at most y % by weight of unsaturated compound(s) (Ia) ($0 < y \leq 0.15$) chosen from 3,3,3-trifluoropropene (HFO-1243zf) and the positional isomers of 2,3,3,3-tetrafluoropropene, such as 1,3,3,3-tetrafluoropropene (Z and E isomers) and 1,1,2,3-tetrafluoropropene, and optionally at most 250 ppm of 3,3,3-trifluoropropyne and/or at most 50 ppm of 1,1,1,2,3-pentafluoropropene (HFO-1225ye).

The SC composition which is particularly preferred comprises at least 99.9% by weight of 2,3,3,3-tetrafluoropropene, at most y % by weight of unsaturated compound(s) (Ia) ($0 < y \leq 0.1$) chosen from 3,3,3-trifluoropropene (HFO-1243zf) and the positional isomers of 2,3,3,3-tetrafluoropropene, such as 1,3,3,3-tetrafluoropropene (Z and E isomers) and 1,1,2,3-tetrafluoropropene, and optionally at most 200 ppm of 3,3,3-trifluoropropyne and/or at most 5 ppm of 1,1,1,2,3-pentafluoropropene (HFO-1225ye).

According to a preferred embodiment of the invention, the SC composition comprises from 99.85 to 99.98% by weight of 2,3,3,3-tetrafluoropropene, from 0.02 to 0.15% by weight of unsaturated compound(s) (Ia) chosen from 3,3,3-trifluoropropene (HFO-1243zf) and the positional isomers of 2,3,3,3-tetrafluoropropene, such as 1,3,3,3-tetrafluoropropene (Z and E isomers) and 1,1,2,3-tetrafluoropropene, and optionally at most 200 ppm of 3,3,3-trifluoropropyne and/or at most 5 ppm of 1,1,1,2,3-pentafluoropropene (HFO-1225ye) and/or at most 400 ppm of compounds (Ib).

The stable composition according to the invention exhibits the advantage of being able to be obtained directly by a process for the manufacture of 2,3,3,3-tetrafluoropropene, optionally after at least one separation stage.

Another subject-matter of the present invention is 2,3,3,3-tetrafluoropropene which has a purity of greater than or equal to 99.8% by weight and less than 100% by weight and which comprises at most 0.2% by weight of unsaturated compounds (Ia), optionally at most 500 ppm of 3,3,3-trifluoropropyne and/or at most 200 ppm of 1,1,1,2,3-pentafluoropropene and/or at most 500 ppm of compounds (Ib).

An additional subject-matter of the present invention is 2,3,3,3-tetrafluoropropene which has a purity of greater than or equal to 99.9% by weight and less than 100% by weight and which comprises at most 0.1% by weight of unsaturated compounds (Ia), optionally at most 200 ppm of 3,3,3-trifluoropropyne and/or at most 5 ppm of 1,1,1,2,3-pentafluoropropene and/or at most 500 ppm of compounds (Ib).

2,3,3,3-Tetrafluoropropene can be obtained from hexafluoropropene (HFP) in at least 4 reaction stages:—(i) hydrogenation of HFP in the presence of a hydrogenation catalyst in a solid phase to give 1,1,1,2,3,3-hexafluoropropane; (ii) dehydrofluorination of the 1,1,1,2,3,3-hexafluoropropane obtained in stage (i) in the liquid phase using an alkali metal hydroxide or in the gas phase in the presence of a dehydrohalogenation catalyst to give 1,1,1,2,3-pentafluoropropene; (iii) hydrogenation of the HFO-1225ye obtained in (ii) in the presence of a hydrogenation catalyst in the solid phase to give 1,1,1,2,3-pentafluoropropane; (iv) dehydrofluorination of the HFC-245eb obtained in stage (iii) in the liquid phase using an alkali metal hydroxide or in the gas phase in the presence of a dehydrohalogenation catalyst to give 2,3,3,3-tetrafluoropropene.

2,3,3,3-Tetrafluoropropene can be obtained from hexafluoropropene (HFP) in at least 2 reaction stages:—(i) hydrogenation of HFP in the presence of a hydrogenation catalyst in the solid phase to give 1,1,1,2,3-pentafluoropropane; (ii) dehydrofluorination of the HFC-245eb obtained in stage (i) in the liquid phase using an alkali metal hydroxide or in the gas phase in the presence of a dehydrohalogenation catalyst to give 2,3,3,3-tetrafluoropropene.

The 2,3,3,3-tetrafluoropropene according to the present invention can be obtained from HFP according to a process as described above after a purification of the HFC-245eb and/or after purification of the 2,3,3,3-tetrafluoropropene.

Thus, the HFC-245eb, prior to the dehydrofluorination stage, is, for example, purified by distillation at an absolute pressure of 6 bar and at a column bottom temperature of 80° C. and a top temperature of 50° C. with approximately 30 theoretical plates and a reflux ratio of approximately 37.

After the final dehydrofluorination stage, the HFO-1234yf is subjected to double distillation. The first distillation is carried out at an absolute pressure of approximately 13 bar, a column bottom temperature of approximately 60° C. and a top temperature of approximately 40° C. and with approximately 35 theoretical plates and a reflux ratio of approximately 500. The second distillation is carried out at an absolute pressure of approximately 11 bar, a column bottom temperature of approximately 105° C., and a top temperature of approximately 44° C. and with approximately 30 theoretical plates at a reflux ratio of approximately 4.

The 2,3,3,3-tetrafluoropropene can also be obtained from 1,1,1-trifluoro-2-chloropropene by hydrofluorination in the liquid or gas phase in the presence of a fluorination catalyst. The 2,3,3,3-tetrafluoropropene thus obtained can be purified to give the 2,3,3,3-tetrafluoropropene according to the present invention.

The compositions according to the present invention are capable of being used as heat transfer agent in stationary or motor-vehicle air conditioning, refrigeration and heat pumps.

Another subject-matter of the present invention is the compositions as described above in combination with a lubricant.

Mention may in particular be made, as lubricant, of polyol esters (POEs), polyalkylene glycols (PAGs), polyalkylene glycol esters and polyvinyl ethers (PVEs).

The PAG lubricants are in the oxyalkylene homo- or copolymer form. The preferred PAGs are homopolymers composed of oxypropylene groups with a viscosity of 10 to 200 centistokes at 40° C., advantageously between 30 and 80 centistokes. The hydroxyl groups at the ends of the oxyalkylene homo- or copolymer chains can be more or less replaced by —O—$C_nH_{2n+1}$ groups where n=1 to 10; the group with n=1 being preferred. The PAGs which may be suitable are those having hydroxyl groups for each ending or —O—$C_nH_{2n+1}$ groups.

Mention may in particular be made, as POEs, of esters of carboxylic acids having a linear or branched carbon chain of 2 to 15 atoms and of polyols having a neopentyl backbone, such as neopentyl glycol, trimethylolpropane, pentaerythritol and dipentaerythritol; pentaerythritol is the preferred polyol. Esters of carboxylic acids having a carbon chain of 4 to 9 atoms are preferred.

Mention may in particular be made, as carboxylic acid of 4 to 9 carbon atoms, of n-pentanoic acid, n-hexanoic acid, n-heptanoic acid, n-octanoic acid, 2-ethylhexanoic acid, 2,2-dimethylpentanoic acid, 3,5,5-trimethylhexanoic acid, adipic acid and succinic acid.

Some alcohol functional groups are not esterified; however, the proportion remains low.

The POE oils selected can comprise between 0 and 5 relative mol % of $CH_2$—OH units with respect to the —$CH_2$—O—(C=O)— units.

The preferred POE lubricants are those having a viscosity of 1 to 1000 centistokes (cSt) at 40° C., preferably of 10 to 200 cSt and advantageously of 30 to 80 cSt.

EXPERIMENTAL PART

The thermal stability trials are carried out according to Standard ASHRAE 97-2007: "sealed glass tube method to test the chemical stability of materials for use within refrigerant systems".

The test conditions are as follows:
Weight of fluid: 2.2 g
Weight of lubricant: 5 g
Temperature: 200° C.
Duration: 14 days Lengths of steel are introduced into tubes.

The length of steel and the lubricant are introduced into a 42.2 ml glass tube. The tube is subsequently evacuated under vacuum and then the fluid F is added thereto. The tube is then welded in order to close it and placed in an oven at 200° C. for 14 days.

At the end of the test, various analyses are carried out:
the gas phase is recovered in order to be analyzed by gas chromatography: the main impurities were identified by GC/MS (coupled gas chromatography/mass spectrometry). The impurities coming from the fluid F and those coming from the lubricant can thus be combined.

the length of steel is weighed (measurement of the rate of corrosion) and observed under a microscope.

the lubricant is analyzed: color (by spectrocolorimetry, Labomat DR Lange LICO220 model MLG131), water content (by Karl Fischer coulometry, Mettler DL37) and acid number (by quantitative determination with 0.01N methanolic potassium hydroxide).

The lubricant used in the tests is a commercial PAG oil: PAG NDB.

The fluid used for these trials comprises essentially HFO-1234yf (at least 99.9% by weight) and then 300 ppm of HFO-1243zf, 500 ppm of E HFO-1234ze and 300 ppm of HFO-1243zf+500 ppm of E HFO-1234ze are respectively added to the fluid.

| Content of | ppm | ppm | ppm | ppm |
| --- | --- | --- | --- | --- |
| E HFO-1234ze added | — | — | 500 | 500 |
| HFO-1243zf added | — | 300 | | 300 |
| Byproducts in the gas phase: | | | | |
| from the HFO-1234yf | 600 ppm | 600 ppm | 900 ppm | 900 ppm |
| from the oil | 1.4% | 1.4% | 1.4% | 1.4% |
| Rate of corrosion | <5 µm/year | <5 µm/year | <5 µm/year | <5 µm/year |
| Analysis of the oil: | | | | |
| color | 10 Gardner | 9 Gardner | 8.5 Gardner | 9 Gardner |
| water content | 300 ppm | 300 ppm | 250 ppm | 300 ppm |
| acid number | 5.2 mg KOH/g | 5.2 mg KOH/g | 4.5 mg KOH/g | 5.2 mg KOH/g |

The examples show that the presence of the compounds (Ia) is not harmful to the thermal stability, either of the HFO-1234yf composition or of the lubricant, and in some cases improves it.

The invention claimed is:

1. A composition comprising a refrigerant comprising from 99.8 to 99.98 wt.% of 2,3,3,3-tetrafluoropropene, from 0.02 to 0.2 wt. % of 3,3,3-trifluoropropene (HFO 1243zf) and at least one positional isomer of 2,3,3,3-tetrafluoropropene selected from the group consisting of 1,3,3,3-tetrafluoropropene (Z and E isomers) and 1,1,2,3-tetrafluoropropene, and optionally at most 500 ppm of 3,3,3-trifluoropropyne and/or at most 200 ppm of 1,1,1,2,3-pentafluoropropene (HFO-1225ye).

2. The composition according to claim 1, wherein the refrigerant further comprises at least one of the compounds (Ib) chosen from 1,1,1,2-tetrafluoropropane (HFC-254eb), 1,1,1,2,3-pentafluoropropane (HFC-245eb), 1,1,1,2-tetrafluoroethane (HFC-134a), 1,1,2-trifluoroethane (HFC-143), 1,1,1,2,3,3-hexafluoropropane, hexafluoropropene, cyclohexafluoropropene, and 1,1,1,3,3-pentafluoropropene (HFO-1225zc).

3. The composition according to claim 2, wherein the compound(s) (Ib) represent(s) at most 500 ppm of the composition.

4. The composition according to claim 3, wherein the compound(s) (Ib) represent(s) at most 400 ppm of the composition.

5. The composition according to claim 1, wherein the refrigerant comprises from 99.85 to 99.98 wt. % of 2,3,3,3-tetrafluoropropene, from 0.02 to 0.15 wt. % of 3,3,3-trifluoropropene (HFO-1243zf) and at least one positional isomer of 2,3,3,3-tetrafluoropropene, and optionally at most 250 ppm of 3,3,3-trifluoropropyne and/or at most 50 ppm of 1,1,1,2,3-pentafluoropropene (HFO-1225ye).

6. The composition according to claim 1, wherein the refrigerant comprises from 99.9 to 99.98 wt. % of 2,3,3,3-tetrafluoropropene, from 0.02 to 0.1 wt. % of 3,3,3-trifluoropropene (HFO-1243zf) and at least one positional isomer of 2,3,3,3-tetrafluoropropene, and optionally at most 200 ppm of 3,3,3-trifluoropropyne and/or at most 5 ppm of 1,1,1,2,3-pentafluoropropene (HFO-1225ye).

7. The composition according to claim 1, wherein the composition is used as a heat transfer agent in stationary or motor-vehicle air conditioning, refrigeration and heat pumps.

8. The composition according to claim 1, wherein the composition further comprises a lubricant.

9. The composition according to claim 8, wherein the lubricant is chosen from polyol esters (POEs), polyalkylene glycols (PAGs), polyalkylene glycol esters and polyvinyl ethers (PVEs).

10. The composition according to claim 1, wherein the refrigerant comprises at most 500 ppm of 3,3,3-trifluoropropyne and/or at most 200 ppm of 1,1,1,2,3-pentafluoropropene (HFO-1225ye).

11. The composition according to claim 1, wherein the refrigerant comprises at most 250 ppm of 3,3,3-trifluoropropyne and/or at most 50 ppm of 1,1,1,2,3-pentafluoropropene (HFO-1225ye).

12. The composition according to claim 1, wherein the refrigerant comprises at most 200 ppm of 3,3,3-trifluoropropyne and/or at most 5 ppm of 1,1,1,2,3-pentafluoropropene (HFO-1225ye).

13. The composition according to claim 1, wherein the refrigerant consists of from 99.8 to 99.98 wt. % of 2,3,3,3-tetrafluoropropene, from 0.02 to 0.2 wt. % of 3,3,3-trifluoropropene (HFO 1243zf) and at least one positional isomer of 2,3,3,3-tetrafluoropropene, and optionally at most 500 ppm of 3,3,3-trifluoropropyne and/or at most 200 ppm of 1,1,1,2,3-pentafluoropropene (HFO-1225ye).

14. The composition according to claim 1, wherein the positional isomer of 2,3,3,3-tetrafluoropropene is the E isomer of 1,3,3,3-tetrafluoropropene.

15. A composition comprising a refrigerant comprising from 99.8 to 99.98 wt. % of 2,3,3,3-tetrafluoropropene and from 0.02 to 0.2 wt. % of 3,3,3-trifluoropropene (HFO 1243zf) and at least one positional isomer of 2,3,3,3-tetrafluoropropene.

16. The composition according to claim 15, wherein the refrigerant further comprises at least one of the compounds (Ib) chosen from 1,1,1,2-tetrafluoropropane (HFC-254eb), 1,1,1,2,3-pentafluoropropane (HFC-245eb), 1,1,1,2-tetrafluoroethane (HFC-134a), 1,1,2-trifluoroethane (HFC-143), 1,1,1,2,3,3-hexafluoropropane, hexafluoropropene, cyclohexafluoropropene, and 1,1,1,3,3-pentafluoropropene (HFO-1225zc).

17. The composition according to claim 16, wherein the compound(s) (Ib) represent(s) at most 500 ppm of the composition.

18. The composition according to claim 17, wherein the compound(s) (Ib) represent(s) at most 400 ppm of the composition.

19. The composition according to claim 15, wherein the composition is used as a heat transfer agent in stationary or motor-vehicle air conditioning, refrigeration and heat pumps.

20. The composition according to claim 15, wherein the composition further comprises a lubricant.

21. The composition according to claim 20, wherein the lubricant is chosen from polyol esters (POEs), polyalkylene glycols (PAGs), polyalkylene glycol esters and polyvinyl ethers (PVEs).

22. The composition according to claim 15, wherein the refrigerant comprises at most 500 ppm of 3,3,3-trifluoropropyne and/or at most 200 ppm of 1,1,1,2,3-pentafluoropropene (HFO-1225ye).

23. The composition according to claim 15, wherein the refrigerant comprises at most 250 ppm of 3,3,3-trifluoropropyne and/or at most 50 ppm of 1,1,1,2,3-pentafluoropropene (HFO-1225ye).

24. The composition according to claim 15, wherein the refrigerant comprises at most 200 ppm of 3,3,3-trifluoropropyne and/or at most 5 ppm of 1,1,1,2,3-pentafluoropropene (HFO-1225ye).

25. The composition according to claim 15, wherein the refrigerant comprises from 99.85 to 99.98 wt. % of 2,3,3,3-tetrafluoropropene, from 0.02 to 0.15 wt. % of 3,3,3-trifluoropropene (HFO-1243zf) and at least one positional isomer of 2,3,3,3-tetrafluoropropene.

26. The composition according to claim 15, wherein the refrigerant comprises from 99.9 to 99.98 wt. % of 2,3,3,3-tetrafluoropropene, from 0.02 to 0.1 wt. % of 3,3,3-trifluoropropene (HFO-1243zf) and at least one positional isomer of 2,3,3,3-tetrafluoropropene.

* * * * *